United States Patent
Khare et al.

(10) Patent No.: US 11,850,053 B2
(45) Date of Patent: Dec. 26, 2023

(54) SYSTEM FOR MEASURING HEART RATE

(71) Applicant: SPORTS DATA LABS, INC., Royal Oak, MI (US)

(72) Inventors: Vivek Khare, Cupertino, CA (US); Viprali Bhatkar, Arlington, MA (US); Mark Gorski, Royal Oak, MI (US); Stanley Mimoto, Bethel Island, CA (US); Anuroop Yadav, Livingston, NJ (US)

(73) Assignee: SPORTS DATA LABS, INC., Royal Oak, MI (US)

( * ) Notice: Subject to any disclaimer, the term of this patent is extended or adjusted under 35 U.S.C. 154(b) by 785 days.

(21) Appl. No.: 16/977,696

(22) PCT Filed: Jan. 14, 2020

(86) PCT No.: PCT/US2020/013461
§ 371 (c)(1),
(2) Date: Sep. 2, 2020

(87) PCT Pub. No.: WO2020/150203
PCT Pub. Date: Jul. 23, 2020

(65) Prior Publication Data
US 2021/0038104 A1   Feb. 11, 2021

Related U.S. Application Data (63) Continuation-in-part of application No. 16/246,923, filed on Jan. 14, 2019.

(51) Int. Cl.
*A61B 5/0245* (2006.01)
*A61B 5/00* (2006.01)
(Continued)

(52) U.S. Cl.
CPC ............ *A61B 5/352* (2021.01); *A61B 5/0022* (2013.01); *A61B 5/0245* (2013.01); *A61B 5/339* (2021.01); *A61B 5/6801* (2013.01); *G06N 20/00* (2019.01)

(58) Field of Classification Search
CPC . A61B 2503/10; A61B 5/0022; A61B 5/0245; A61B 5/332; A61B 5/339;
(Continued)

(56) References Cited

U.S. PATENT DOCUMENTS 4,938,228 A   7/1990   Righter et al.
6,080,110 A   6/2000   Thorgersen
(Continued)

OTHER PUBLICATIONS

Ramos et al. (Real-Time Approach to HRV Analysis, 2018) (Year: 2018).*
(Continued)

*Primary Examiner* — Scott Luan
(74) *Attorney, Agent, or Firm* — Brooks Kushman P.C.

(57) ABSTRACT

A method of computing a heart rate value compensates for noise derived from the subject, the sensor, the transmission, and/or other variables that can lead to false R-peak detection or missed R-peak detection. The method computes an updated heart rate based on a window of approximately ten seconds of digitized ECG readings broadcast from a sensor. A new value is calculated approximately every second such that the window of ECG readings overlaps considerably between consecutive calculations. The method compensates for noisy data by discarding heart rate samples that differ by more than a threshold amount from a previously calculated heart rate value. The threshold is adjusted based on a standard deviation of differences between heart rate samples. Prior to calculating a heart rate value, a forward-looking, pre-filter logic may be applied in situations where the raw data has an extremely low signal-to-noise ratio.

26 Claims, 5 Drawing Sheets

(51) Int. Cl.
*G06N 20/00* (2019.01)
*A61B 5/352* (2021.01)
*A61B 5/339* (2021.01)

(58) Field of Classification Search
CPC ..... A61B 5/352; A61B 5/6801; A61B 5/7203; G06N 20/00; G06N 3/045; G06N 3/088
See application file for complete search history.

(56) References Cited

U.S. PATENT DOCUMENTS

| | | |
|---|---|---|
| 2004/0228217 A1 | 11/2004 | Szeto |
| 2007/0219455 A1 | 9/2007 | Wong et al. |
| 2012/0130263 A1 | 5/2012 | Pretorius et al. |
| 2012/0271185 A1 | 10/2012 | Sanghera et al. |
| 2013/0303922 A1 | 11/2013 | Buchheim et al. |
| 2014/0073979 A1 | 3/2014 | Inciardi et al. |
| 2014/0275960 A1 | 9/2014 | Hubbard |
| 2015/0164410 A1 | 6/2015 | Selvaraj et al. |
| 2016/0213261 A1 | 7/2016 | Fleischer et al. |
| 2018/0078219 A1 | 3/2018 | Selvaraj |
| 2018/0103855 A1 | 4/2018 | Dunbar et al. |
| 2018/0125385 A1 | 5/2018 | Chauhan et al. |
| 2018/0242876 A1 | 8/2018 | Hughes et al. |
| 2020/0221958 A1 | 7/2020 | Bhatkar et al. |
| 2020/0253476 A1 | 8/2020 | Khare et al. |
| 2021/0015079 A1 | 1/2021 | Gorski et al. |

OTHER PUBLICATIONS

Non-final Office Action dated Feb. 17, 21 for U.S. Appl. No. 16/246,923, filed Jan. 14, 2019, 14 pgs.
Non-final Office Action dated Jun. 8, 2022 for U.S. Appl. No. 16/246,923, 9 pgs.
Tetelepta, S., "Exploring Heart Rate Variability Using Python," published in Orikami blog Aug. 28, 2018, https://medium.com/orikami-blog/exploring-heart rate-variability using-python-483a7037c64d, 16 pgs.
European Search Report & Written Opinion dated Nov. 30, 22 for European Appn. No. 20742114.0, 14 pgs.
International Search Report dated Apr. 22, 2020 for PCT Appn. No. PCT/US20/13461, 9 pgs.
Pavlatos, C. et al., "Hardware Implementation of Pan & Tompkins QRS Detection Algorithm," Proceedings of EMBEC05 Conference, 2005, 5 pgs.
Non-final Office Action dated Jun. 23, 2021 for U.S. Appl. No. 16/246,923, filed Jan. 14, 2019, 8 pgs.
Non-final Office Action dated Jul. 13, 2023 for U.S. Appl. No. 16/246,923, 21 pgs.
Partial Search Report & Written Opinion dated Sep. 1, 2022 for European Appn. No. 20742114.0, 13 pgs.

\* cited by examiner

SYSTEM FOR MEASURING HEART RATE

CROSS-REFERENCE TO RELATED APPLICATIONS

This application is the U.S. national phase of PCT Appln. No. PCT/US2020/01346 filed Jan. 14, 2020 which is a continuation-in-part of U.S. patent application Ser. No. 16/246,923 filed Jan. 14, 2019, the disclosure of which is hereby incorporated in its entirety by reference herein.

TECHNICAL FIELD

This disclosure relates to the field of human data monitoring systems. More particularly, the disclosure pertains to a system for measuring a heart rate, for example of a person engaged in sports or other highly active and mobile activity.

BACKGROUND

Heart Rate (HR) is a key indicator of the function and performance of the heart during various activities. A real-time HR computation reflects beat by beat changes in HR due to underlying physical and/or mental activities. The changes in HR can be captured as Heart Rate Variability (HRV) and are very important in the diagnosis and monitoring of the heart health. Displaying an instantaneous HR during such activities provides important information about heart health as well as the effect of the underlying activity.

Heart rate computations can be adversely affected by the motion artifacts induced in the Electrocardiogram (ECG) signal due to body movements. Some of these changes can be filtered out but when there are no R-peaks identified, sudden increase or decrease in the HR may be observed. Such frequent noisy periods in the raw signal can lead to a noisy HR waveform.

SUMMARY OF THE DISCLOSURE

In one aspect, a system for measuring a heart rate is provided The system includes at least one sensor, a server, and a display device. The at least one sensor is configured to measure electric signals in the subject's body, convert analog measurements to digital readings, and transmit the digital readings. The server receives the digital readings and calculates the one or more heart rate values based on overlapping segments of the digital readings by (i) identifying R-peaks within the overlapping segments, (ii) calculating a number of sample values based on times between adjacent R-peaks, (iii) discarding samples that are influenced by false peak detection or missed peak detection, and (iv) calculating an average, which may be weighted, of remaining sample values. The display device communicates the calculation of the remaining sample values to one or more users. The server may determine that samples are influenced by false peak detection or missed peak detection in response to a sample value differing from a previous heart rate value by more than a first threshold. If a standard deviation of differences between samples is greater than a second threshold, the server may determine that samples are influenced by false peak detection or missed peak detection in response to the sample value differing from the previous heart rate value by more than a third threshold less than the first threshold.

In another aspect, a system for measuring a heart rate is provided. The system includes at least one sensor configured to measure electric signals in a subject's body, convert one or more analog measurements to one or more digital readings, and transmit the one or more digital readings. A server is configured to receive the one or more digital readings and calculate heart rate based on one or more overlapping segments of the one or more digital readings by identifying R-peaks within the one or more overlapping segments, calculating one or more sample values based on times between adjacent R-peaks, discarding one or more samples that are influenced by false peak detection or missed peak detection, and calculating one or more averages of remaining sample values. The system also includes a display device configured to display the one or more averages of the remaining sample values.

In another aspect, a system for measuring a heart rate is provided. The system includes includes at least one sensor, a server, and a display device. The at least one sensor is adapted for fixation to a subject's skin and configured to measure electric signals in the skin, convert analog measurements to digital readings, and transmit the digital readings. The server receives the digital readings and calculates the one or more heart rate values based on one or more overlapping segments of the digital readings by (i) identifying R-peaks within the one or more overlapping segments, (ii) calculating a number of sample values based on times between adjacent R-peaks, (iii) selecting samples within a first threshold of a previous heart rate value, and (iv) setting a current heart rate value to an average of the selected samples, which may be weighted. Each sample value may be proportional to a reciprocal of a time between adjacent R-peaks. The server may select samples within a second threshold of the previous heart rate value in response to a standard deviation of differences between consecutive samples being greater than a third threshold. The server may set the current heart rate value equal to the previous heart rate value in response to the number of samples being less than a fourth threshold or in response to no samples being selected. The display device communicates the one or more current heart rate values to one or more users. The system may operate in real-time or near real-time wherein the display device is configured to display each current heart rate value before a respective succeeding heart rate value is calculated and the server calculates each current heart rate value before the sensor completes measuring at least a portion of or all of the readings used to calculate the succeeding heart rate value. The server may compute an initial heart rate value by receiving a preliminary segment of the digital readings longer than the overlapping segments, identifying R-peaks within the preliminary segment, calculating sample values based on times between adjacent R-peaks, and calculating an average of the samples, which may be weighted.

In still another aspect, a system for measuring a heart rate is provided. The system includes at least one sensor adapted for fixation to, or is in contact with, or sends an electronic communication in relation to or derived from, a subject's skin, vital organ, muscle, veins, blood, blood vessels, tissue, or skeletal system and configured to measure one or more electric signals in subject's body, convert analog measurements to one or more digital readings, and transmit the digital readings. A server is configured to receive the one or more digital readings and calculate one or more heart rate values based on one or more overlapping segments of the one or more digital readings by identifying R-peaks within the one or more overlapping segments, calculating one or more sample values based on times between adjacent R-peaks, selecting one or more samples within a first threshold of a previous heart rate value, and setting a current heart rate value to an average of selected samples. The system also includes a display device configured to display one or more current heart rate values.

In still another aspect, a method for measuring a heart rate of one or more persons is provided. The method includes a step of receiving readings from at least one sensor, processing the readings, and displaying the one or more results. A first segment of readings is received from the one or more sensors. R-peaks within the first segment are then identified. Then, a first plurality of sample values is calculated based on times between adjacent R-peaks. For example, a constant may be divided by times between adjacent R-peaks. A first subset of the first plurality of sample values are selected including only sample values within a first threshold of a previous heart rate value. Then, a first updated heart rate value is calculated based on an average of the first subset of sample values. The first updated heart rate value is then displayed. In later iterations, a second segment of the digital readings may be received from the one or more sensors. A third segment of digital readings may be formed by appending the second segment to the first segment. R-peaks within the third segment may then be identified. A second plurality of sample values may be calculated based on times between adjacent R-peaks. Then, a plurality of differences between consecutive samples may be calculated. In response to a standard deviation of the differences exceeding a second threshold, a second subset of the second plurality of sample values may be selected including only sample values within a third threshold of the first updated heart rate value. A second updated heart rate value may then be calculated and displayed based on an average of the second subset of sample values, which may be weighted. An initial heart rate value may be calculated based on a preliminary segment of the digital readings.

In still another aspect, issues related to signal quality are addressed. In cases where the raw data has an extremely low signal-to-noise ratio, additional pre-filter logic may be applied prior to calculating a heart rate value. The pre-filter process detects any outlier values and replaces the one or more outlier values, using a look-ahead approach, with values that align in the time series of generated values and fit within a preestablished threshold/range. These generated values that fit within a preestablished threshold/range will be passed along through the system for its computation of the one or more heart rate values.

In yet another aspect, a method for detecting and replacing one or more outlier values generated from one or more sensors is provided. The method includes a step of receiving one or more values generated directly or indirectly by the one or more sensors. One or more statistical tests are applied to determine an acceptable upper and/or lower bound for each value. A backward filling method is used to replace the one or more outlier values with a next available value that falls within an acceptable range established in a current window of samples.

DETAILED DESCRIPTION

Embodiments of the present disclosure are described herein. It is to be understood, however, that the disclosed embodiments are merely examples and other embodiments can take various and alternative forms. The figures are not necessarily to scale; some features could be exaggerated or minimized to show details of particular components. Therefore, specific structural and functional details disclosed herein are not to be interpreted as limiting, but merely as a representative basis for teaching one skilled in the art to variously employ the present invention. As those of ordinary skill in the art will understand, various features illustrated and described with reference to any one of the figures can be combined with features illustrated in one or more other figures to produce embodiments that are not explicitly illustrated or described. The combinations of features illustrated provide representative embodiments for typical applications. Various combinations and modifications of the features consistent with the teachings of this disclosure, however, could be desired for particular applications or implementations.

It must also be noted that, as used in the specification and the appended claims, the singular form "a," "an," and "the" comprise plural referents unless the context clearly indicates otherwise. For example, reference to a component in the singular is intended to comprise a plurality of components.

The term "comprising" is synonymous with "including," "having," "containing," or "characterized by." These terms are inclusive and open-ended and do not exclude additional, unrecited elements or method steps.

The phrase "consisting of" excludes any element, step, or ingredient not specified in the claim. When this phrase appears in a clause of the body of a claim, rather than immediately following the preamble, it limits only the element set forth in that clause; other elements are not excluded from the claim as a whole.

The phrase "consisting essentially of" limits the scope of a claim to the specified materials or steps, plus those that do not materially affect the basic and novel characteristic(s) of the claimed subject matter.

With respect to the terms "comprising," "consisting of," and "consisting essentially of," where one of these three terms is used herein, the presently disclosed and claimed subject matter can include the use of either of the other two terms.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100. Similarly, when any range is called for, intervening numbers that are increments of the difference between the upper limit and the lower limit divided by 10 can be taken as alternative upper or lower limits. For example, if the range is 1.1, to 2.1 the following numbers 1.2, 1.3, 1.4, 1.5, 1.6, 1.7, 1.8, 1.9, and 2.0 can be selected as lower or upper limits.

The term "server" refers to any computer, computing device, mobile phone, desktop computer, notebook computer or laptop computer, distributed system, blade, gateway, switch, processing device, or combination thereof adapted to perform the methods and functions set forth herein.

Figure 1:
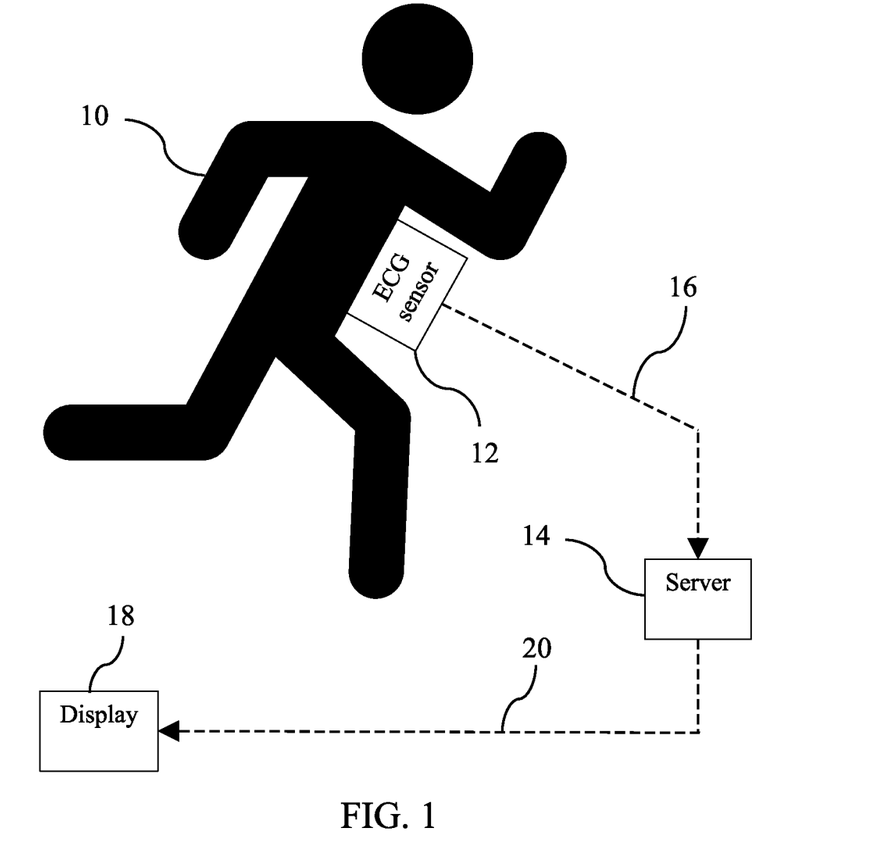
FIG. 1 is a schematic diagram of a heart rate measurement and display system.

FIG. 1 illustrates a system for determining and displaying a heart rate of subject 10. Typically, subject 10 is a person. However, the subject may be any living being from which ECG-related data can be derived (e.g., animals). In a refinement, a subject includes one or more digital representations of a living being (e.g., a data set that represents a human or animal that is artificially created and shares at least one common characteristic with a human or animal), and one or more artificial creations that share one or more characteristics with a human or other animal (e.g., lab-grown heart that produce one or more electrical signals similar to that of a human or animal heart). Advantageously, the subject is active, such as a person engaged in a sport or movement (e.g., construction workers, soldiers, individuals walking, individuals in a fitness class). However, the system for determining and displaying a heart rate can be used for any subject engaged in any activity (e.g., sleeping, sitting). Depending on the nature of the activity, the subject's heart rate may vary considerably over relatively short time frames. At least one ECG sensor 12 and/or its one or more appendices are attached to, or embedded within, the subject 10 and measures electrical changes in the subject's body (e.g., skin) associated with heart function. In a refinement, the at least one ECG sensor and/or its one or more appendices may be affixed to, are in contact with, or send an electronic communication in relation to or derived from, the subject including a subject's skin, eyeball, vital organ, or skeletal system, lodged in a subject, ingested by a subject, or integrated into or as part of, affixed to or embedded within, a textile, fabric, cloth, material, fixture, object, or apparatus that contacts or is in communication with a subject either directly or via one or more intermediaries. Examples include an ECG sensor that sticks to the subject via an adhesive (thus acting as an intermediary between the sensor and the subject), an ECG sensor integrated or embedded into a shirt worn by the subject, an ECG sensor integrated into a steering wheel which is in contact with the subject, an ECG sensor integrated into a video game controller, an ECG sensor connected to a pair of glasses and in contact with the subject's ear, an ECG sensor integrated into fitness equipment, and the like. Advantageously, an ECG sensor may have multiple sensors within a single sensor. In a refinement, the at least one ECG sensor has other sensing capabilities that enable the at least one sensor to provide non-ECG related data. For example, an ECG sensor may also have a gyroscope, accelerometer, and magnetometer capable of capturing and providing XYZ coordinates.

The at least one sensor digitizes the one or more measurements and transmits the digitized measurements to a server 14. The digitized measurements may be sent to a server using one or more wireless communication protocols 16. While the present invention is not limited by the technologies that sensors use to transmit its signals, such wireless communication protocols that may be utilized include Bluetooth, Zigbee, Ant+, and Wifi. In a refinement, the server is integrated within or as part of, affixed to, or combined with the sensor as a single unit or a unit with one or more appendices, which may transmit the digitalized measurements through a wired or wireless connection. For example, the sensor collecting one or more digitalized measurements may be a watch, and the server may be located within the encasing of the watch or integrated within the one or more watch components that comprise the watch. In another example, the sensor collecting one or more digitalized measurements and the server may be located within the encasing of eyewear, attached to the eyewear, or integrated within the one or more eyewear components that comprise the eyewear.

The one or more communication protocols may be direct or may involve one or more intermediary devices in order for the measurements to reach the server in real-time or near real-time. For example, one or more transmission subsystems may be utilized to transmit the digitalized measurements to server 14. A transmission subsystem includes a transmitter and a receiver, or a combination thereof (e.g., transceiver). A transmission subsystem can include receivers, transmitters and/or transceivers having a single antenna or multiple antennas, which may be part of a mesh network. In a refinement, the transmitter, receiver, or transceiver is integral to the at least one or more ECG sensors. In another refinement, the one or more transmission subsystems may be wearable and may be affixed to, or in contact with, the subject either directly or via one or more intermediaries (e.g., clothing, equipment worn by a person). In yet another refinement, the one or more transmission subsystems includes an on or in-body transceiver ("on-body transceiver") that optionally acts as another sensor or is integrated within the at least one ECG sensor. The on-body transceiver is operable to communicate with the at least one ECG sensor on a targeted subject or across one or more target subjects, and may track one or more types of other biological data in addition to ECG-related data (e.g., location data, hydration data, biomechanical data). In a refinement, the on-body transceiver is affixed to, integrated or in contact with, a subject's skin, vital organ, muscle, skeletal system, clothing, object, or other apparatus on the subject's body. Advantageously, the on-body transceiver collects data in real-time or near real-time from one or more ECG sensors on a subject's body, communicating with each sensor using the one or more transmission protocols of that particular sensor. In a variation, transmission subsystem may be comprised of, or include, an aerial transceiver for continuous streaming from the at least one ECG sensor on persons or objects. Examples of aerial-based transmission subsystems include, but are not limited to, one or more unnamed aerial vehicles, which may include drones and/or communications satellites, with attached transceivers. Additional details of unmanned aerial vehicle-based data collection and distribution systems are disclosed in U.S. patent Ser. No. 16/517,012 filed Jul. 19, 2019; the entire disclosure of which is hereby incorporated by reference.

Preferably, between 250 and 1000 such measurements are broadcast (e.g., sent) per second, although measurements may be increased or decreased depending on the at least one sensor used. From these measurements, the server 14 computes a heart rate value approximately once per second, although this may be a tunable parameter. The server 14 communicates the one or more heart rate values to a display 18 using a protocol 20. Typically, a display communicates information in visual form. A display may include a plurality of displays that comprise the display. The display may be arranged to be viewed by the subject 10 and/or by others. Advantageously, the display may communicate information utilizing one or more other mechanisms including via an audio or aural format (e.g., verbal communication of a heart rate measurement), via a physical gesture (e.g., a physical vibration which provides information related to the one or more heart rate measurements), or a combination thereof. Protocol 20 may be a wireless protocol or a wired protocol. In some embodiments, the display 18 and the server 14 may be integrated into a single physical device such as a smartphone with processing and display capabilities, or other computing device (e.g., AR/VR headset). The term "computing device" refers generally to any device that can perform at least one function, including communicating with another computing device. In a refinement, a computing device includes a central processing unit that can execute program steps and memory for storing data and a program code. Advantageously, the server 14 and/or the display 18 may be wearable by the person 10 (e.g., smart eyewear, watch).

Figure 2:
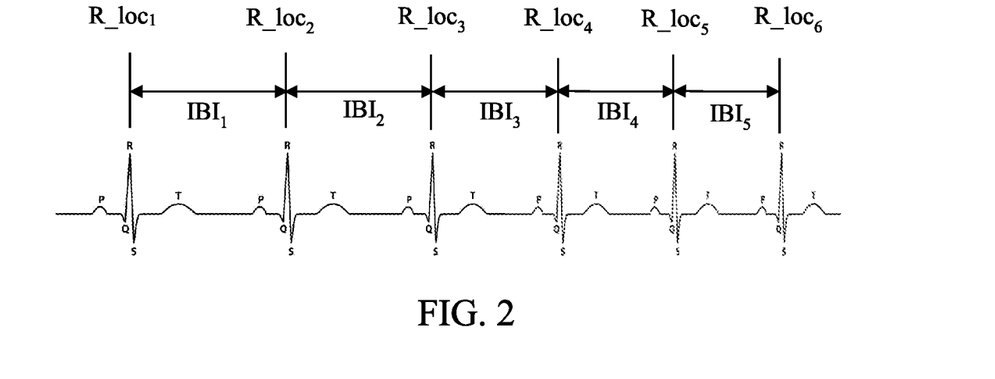
FIG. 2 is a graph illustrating ECG measurements for a person with an increasing heart rate.

FIG. 2 illustrates an exemplary output of the ECG measurements. Note that the measurements follow a regular pattern that repeats for each heart beat. Various points in the repeating pattern are labelled P, Q, R, S, and T. The R point is indicated by a localized peak. The time of the R peaks are labelled $R\_loc_i$ for $1 \leq i \leq n$. The difference between successive $R\_loc$ times are labelled Inter-Beat Interval i ($IBI_i$) for $1 \leq i < n$. (For the output illustrated in FIG. 2, n=6.) Note that the time between R peaks is shorter near the end of the time period illustrated in FIG. 2 than near the beginning of the interval. This indicates that the individual's heart rate is increasing. Calculating the heart rate when the heart rate is rapidly changing is more difficult than calculating it when the heart rate is steady. Although the graph of FIG. 2 shows very distinct R peaks, actual measurements are not necessarily so clear. In the system of FIG. 1, there are a variety of sources of noise in the ECG signal, such as measurement noise from movement of the person's body, noise from artifacts on a person or part of a person (e.g., body muscle, body fat), sensor degradation, conductivity, environmental conditions, and transmission.

One of the ways abnormalities in an instantaneous HR can be handled is by a windowing method. A detailed description of the method is described in the sections below. A sliding window of a certain duration such as 10-sec (or less) to 5-minutes (or more) can be used to look at the ECG data. It contains several detected R-peaks (beats). In a noisy signal, some of these beats could be noise peaks resulting in a very high or low HR outliers. By analyzing the distribution of these values, it is possible to accept or reject a good beat before the HR computations. For the finer resolution and to use the past HR information, overlapping sliding windows can be used. This method is very useful and effective in avoiding abrupt changes in HR. In a refinement, the precise duration of the sliding window is a tunable parameter and may be adjusted based upon artificial intelligence or machine learning techniques that look at previously collected data sets to predict future occurrences, which may be based on one or more parameters including the subject, the activity the subject is engaged in, the sensor, and/or a combination thereof.

Figure 3:
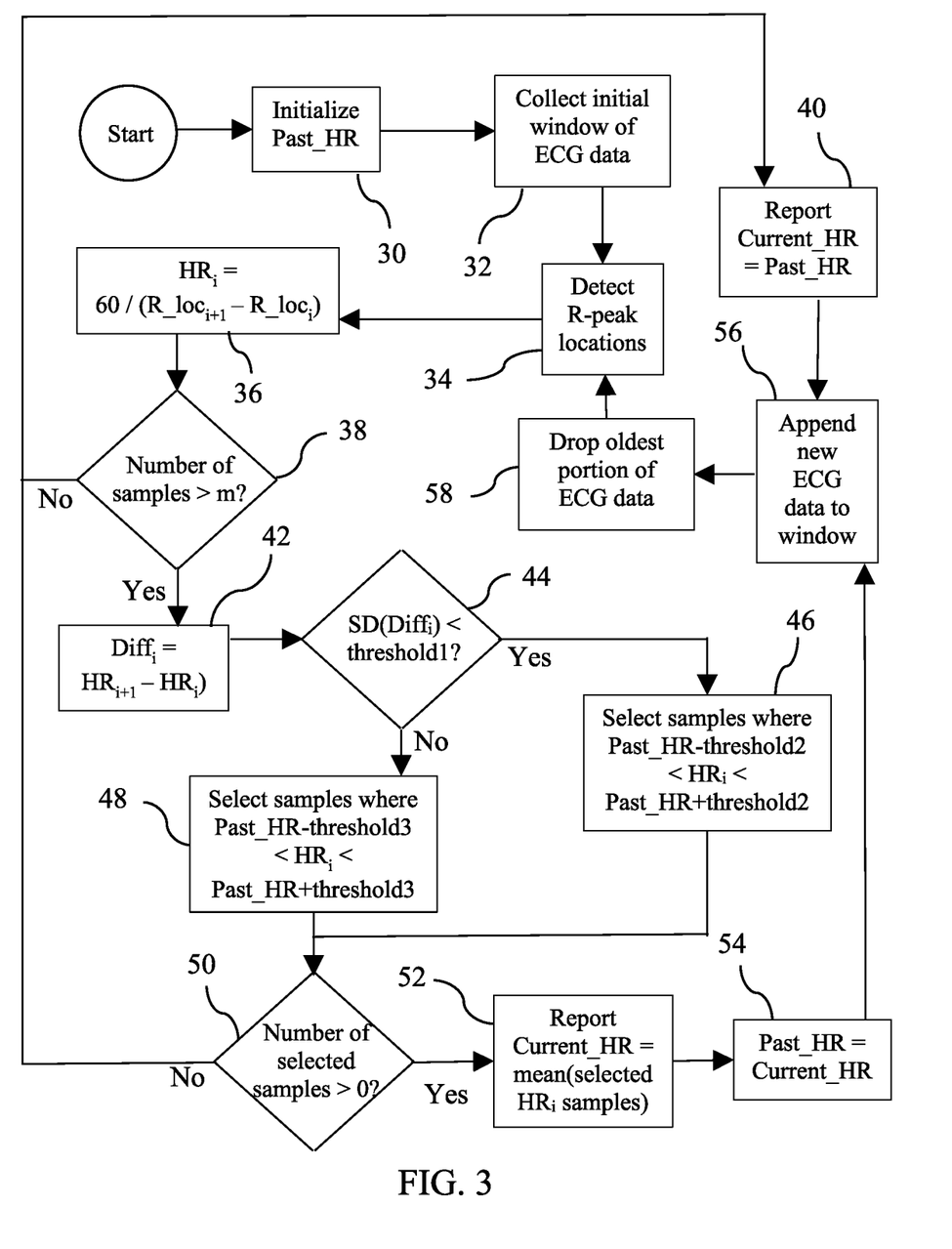
FIG. 3 is a flow chart for a method of calculating a heart rate value based on a stream of digitized ECG measurements in the system of FIG. 1.

FIG. 3 illustrates a method, executed by server 14, of computing a stream of heart rate values based on the received stream of digitized ECG measurements. The method utilizes a parameter, Past_HR, representing the most recently calculated heart rate value. At 30, this parameter is initialized. The procedure for initializing Past_HR is described in more detail below. At 32, the method collects approximately ten seconds of ECG data. The precise duration of data to collect is a tunable parameter. Using a longer period may make the method less responsive to rapid changes in heart rate. Using a period that is too short may increase the frequency of the method not computing an updated heart rate. In a refinement, artificial intelligence or machine learning techniques may be utilized to identify one or more patterns, or weight one or more values, that may enable a longer period or shorter period to be utilized without impacting the one or more heart rate values. At 34, the R-peak locations are identified. Various methods are known for this step, including the Pan-Thompkins algorithm which is a recommended method by the inventors. The result of this step is a series of times, $R\_loc_i$, $1 \leq i \leq n$. At 36, the method calculates a number of sample values based on the time between adjacent $R\_loc$ values. Specifically, each sample value, $HR_i$ for $1 \leq i < n-1$, is equal to 60 divided by the time difference between adjacent $R\_loc$ values. The $HR_i$ sample values have the same units, beats per minute, as the subject's heart rate and would be expected to fall in the same general range. Some embodiments may use different but related sample values, such as IBI, with appropriate conversions before reporting. At 38, the method tests whether the number of samples exceeds a predefined minimum, such as 10. The required number of samples is a tunable parameter. If an insufficient number of samples is available, then the method branches to 40 and reports the previous value without computing an updated value. In a refinement, one or more samples may be artificially generated (created) based upon at least a portion of the previously collected data in order for an updated value to be computed. The artificial data may be generated utilizing one or more artificial intelligence and/or machine learning techniques, which may involve the training of one or more neural networks. Additional details of a System for Generating Simulated Animal Data And Models are disclosed in U.S. Pat. No. 62/897,064 filed Sep. 6, 2019; the entire disclosure of which is hereby incorporated by reference and applicable to other references and examples utilizing one or more artificial intelligence and machine learning techniques in this disclosure.

Two types of peak detection errors may occur due to noise in the received time series of digitized ECG measurements. The first type of error is when a true peak is not detected. The consequence of this type of error is an IBI value equal to the sum of two correct IBI values. The resulting $HR_i$ value will be substantially smaller than the correct heart rate. The second type of error is when a false peak is detected. The consequence of this type of error is two IBI values that add up to a correct IBI value. The resulting two $HR_i$ values are each larger than a correct heart rate. For either type of error, the resulting false values should not be included in the calculation of a reported heart rate value.

If the number of samples is sufficient, the method selects a subset of the samples that are within a threshold of Past_HR. The threshold is dependent upon the standard deviation of the differences of the samples. At 42, the differences between adjacent samples, $Diff_i$ for $1 \leq i < n-2$, are calculated. At 44, the standard deviation of the differences in $HR_i$ samples is computed and compared to a first threshold. The inventors recommend a value of 5 beats per minute for this first threshold, although this is a tunable parameter. If the standard deviation is less than the first threshold, then samples are selected at 46 based on whether or not they are within a second threshold of Past_HR. The inventors recommend a value of 20 beats per minute for this second threshold, although this is a tunable parameter. If the standard deviation is greater than or equal to the first threshold at 44, then samples are selected at 48 based on whether or not they are within a third threshold of Past_HR. The inventors recommend a value of 12 beats per minute for this third threshold, although this is a tunable parameter. At 50, the method tests whether any samples have been selected. If not, then the method branches to 40 and reports the previous value without computing an updated value.

If some samples are selected at 50, then the method computes the Current_HR at 52 by taking an average, preferably the mean, of the selected samples. This updated heart rate value is then reported by transmitting it to the display unit. At 54, Past_HR is set equal to Current_HR. The updated value will be the basis for selecting samples in future iterations.

After reporting either an updated value at 54 or reporting a previous value at 40, the method collects approximately one second of additional ECG data at 56 and appends the additional data to the end of the current ECG data window, which may be called a segment. At 58, the oldest portion of ECG data, equal in duration to the data added at 56, is dropped from the ECG data window. The time interval at 56 and 58 may be adjusted if values are desired more or less frequently. As a result, approximately 90% of the data from the previous iteration is included in the new ECG data window.

Figure 4:
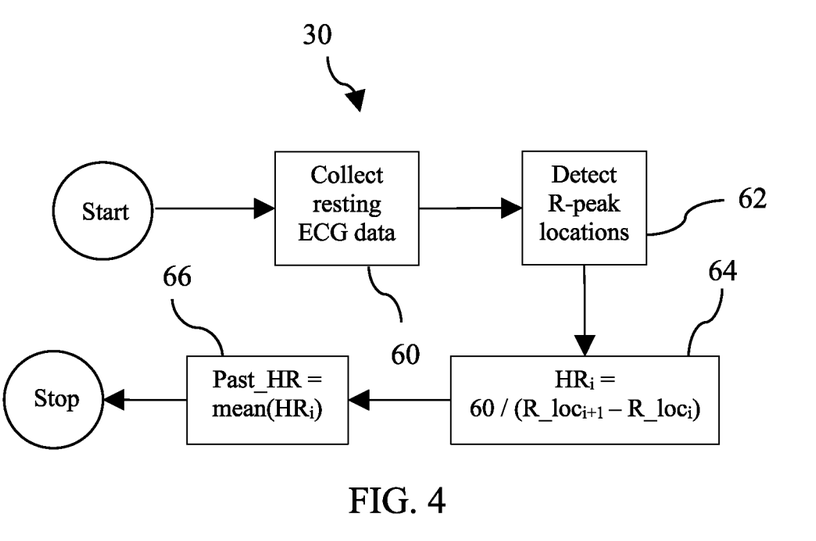
FIG. 4 is a flow chart for performing the initialization step in the method of FIG. 3.

FIG. 4 describes the initialization procedure of step 30. At 60, approximately two minutes of ECG data is collected by the server. However, this is a tunable parameter. Preferably, this data is collected while the person is at rest so that the heart rate is relatively constant and the person's motion does not lead to increased signal noise. At 62, the method identifies the R peaks in the collected stream of ECG measurements using, for example, the Pan-Thompkins algorithm. At 64, a number of sample $HR_i$ values are computed from the times of the R peaks, $R\_loc_i$. At 66 the initial Past_HR value is computed by taking an average of the sample of $HR_i$ values.

Figure 5A:
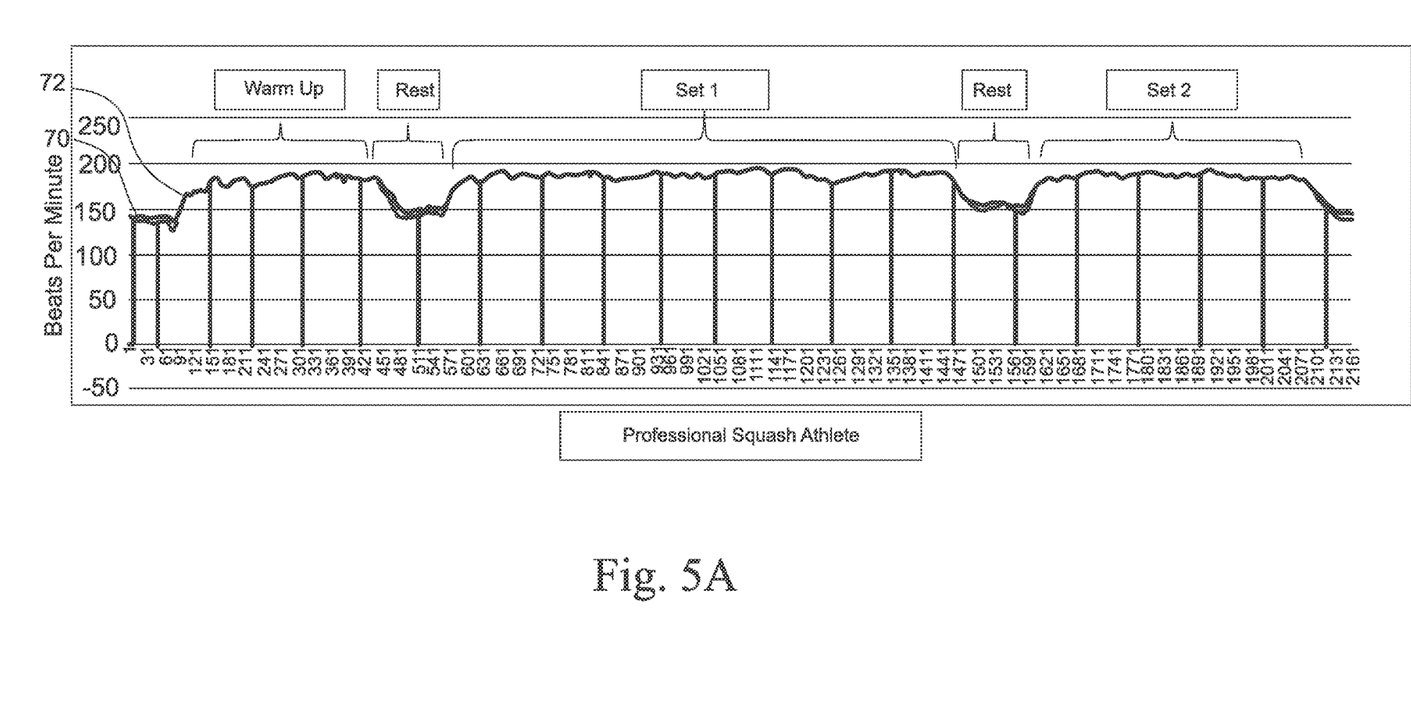
FIGS. 5A and 5B illustrate heart rate measurements of persons engaged in a variety of physical activities utilizing the system and methods described herein.
Figure 5B:
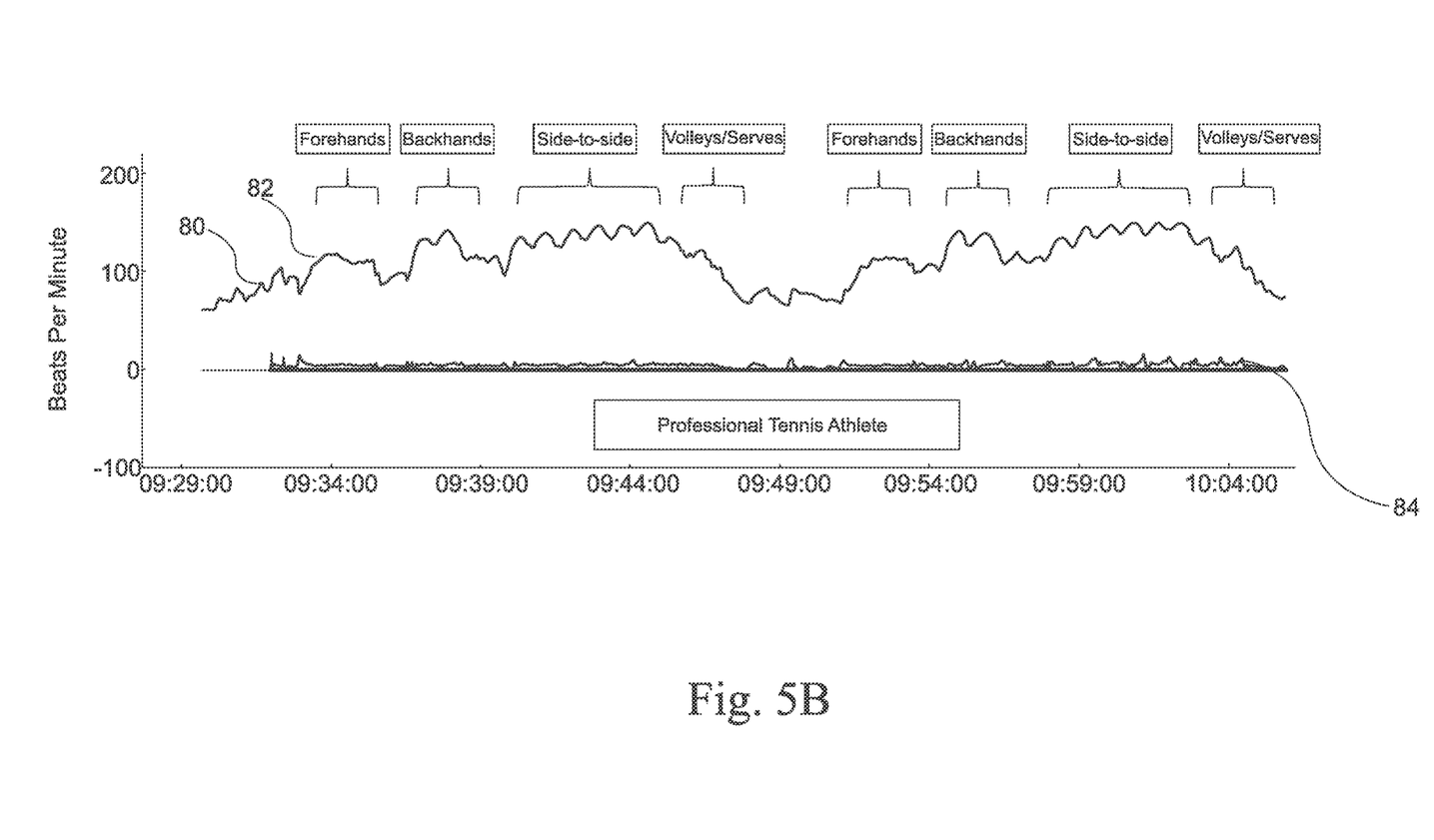

FIGS. 5A and 5B illustrate heart rate measurements of persons engaged in a variety of physical activities utilizing the system and method described herein. In these examples, a single lead sensor that is affixed to a subject's chest via an adhesive generates raw data (e.g., analog measurements) at a sampling rate of 250 measurements per second, which is converted into heart rate measurements utilizing the system and method described herein. FIG. 5A illustrates a comparison of heart rate measurements for the sport of squash, a sport which involves high-activity movement of the human body. Line 70 demonstrates the heart rate measurements derived from a chest-strap based heart rate monitor for a professional squash athlete during a match, while line 72 demonstrates the heart rate measurements of the professional squash athlete during the same match and utilizing the system and method described herein via a single lead sensor. FIG. 5B illustrates a comparison of heart rate measurements for the sport of tennis, a sport which involves high-activity movement of the human body. Line 80 demonstrates the heart rate measurements derived from a chest-strap based heart rate monitor for a professional tennis athlete during a training session, while line 82 demonstrates the heart rate measurements of the professional tennis athlete during the same training session and utilizing the system and method described herein via a single lead sensor. Line 84 demonstrates the delta difference in heart beats per minute between line 80 and line 82.

In a refinement, two or more sensors may be utilized simultaneously or in succession to provide the requisite ECG-related readings to calculate one or more heart rate measurements. For example, in calculating the heart rate measurements, one sensor may be placed in the Lead I position, another sensor may be placed in the Lead II position, and another sensor may be placed in the Lead III position, with two or more of the sensors communicating with a server, with each other, or both, to calculate the one or more heart rate measurements from at least a portion of the data sent by the one or more sensors.

In most cases, the one or more sensors produce analog measurements (e.g., raw AFE data) that are provided directly to server, with the server applying the previously described methods to filter the data and generate one or more heart rate values. However, in cases where data has an extremely low signal-to-noise ratio, pre-filter logic may be required. The inventors propose a pre-filter method whereby the system may take a number of steps to "fix" the data generated from the sensor to ensure that the one or more data values generated are clean and fit within a predetermined range. This pre-filter logic would consume the data from the sensor, detect any outlier or "bad" values, replace these values with expected or "good" values and pass along the "good" values for its computation of the one or more heart rate values. By "fix," the inventors are referring to an ability to create one or more alternative data values (i.e., "good" values) to replace values that may fall out of a preestablished threshold, with the one or more "good" data values aligning in the time series of generated values and fitting within a preestablished threshold. These steps would occur prior to the heart rate logic taking action upon the received data to calculate the one or more HR values.

Advantageously, the pre-filter logic and methodology for identification and replacement of one or more data values can be applied to any type of sensor data collected, including both raw and processed outputs. For illustration purposes, and while raw data such as analog measurements (AFE) can be converted into other wave forms such as electromyography (EMG) signals, the inventors will focus on its conversion to ECG and HR values.

As previously described, the pre-filter logic becomes important in a scenario whereby the signal-to-noise ratio in the time series of generated AFE values from one or more sensors is at or close to zero, or numerically small. In this case, the system and method described herein to generate one or more heart rate values may ignore one or more such values, which may result in no heart rate value generated or a generated heart rate value that may fall outside the pre-established parameters, patterns and/or thresholds. Such AFE values may result from the subject taking an action that increases one or more other physiological parameters (e.g., muscle activity), or in competing signals derived from the same sensor being introduced or deteriorating the connection, or from other variables. This in turn may make for an inconsistent HR series.

To solve for this problem, the inventors have established a method that enables the creation of one or more data values by looking at future values rather than previously generated values. More specifically, the system may detect one or more outlier signal values and replace outlier values with one or more signal values that fall within an expected range (e.g., the established upper and lower bounds), thus having the effect of smoothing the series while at the same time decreasing the variance between each value. The established expected range may take into account a number of different variables including the individual, the type of sensor, one or more sensor parameters, one or more of the sensor characteristics, one or more environmental factors, one or more characteristics of the individual, activity of the individual, and the like. The expected range may also be created by one or more artificial intelligence or machine learning techniques that uses at least a portion of previously collected sensor data and/or its one or more derivatives, and possibly one or more of the aforementioned variables, to predict what an expected range may be. The expected range may also change over a period of time and be dynamic in nature, adjusting based on one or more variables (e.g., the activity the person is engaged in or environmental conditions). In a variation, one or more artificial intelligence or machine learning techniques may be utilized, at least in part, to generate one or more artificial signal values within the expected range (e.g., upper and lower bound) derived from at least a portion of collected sensor data and/or its one or more derivatives from the one or more sensors.

To achieve the desired outcome of creating one or more values based upon future values, the system first samples one or more of the sensor's "normal" or "expected" AFE values and applies statistical tests and exploratory data analysis to determine the acceptable upper and lower bound of each AFE value generated by the sensor, which may include outlier detection techniques like interquartile range (IQR), distribution and percentile cut offs, kurtosis, and the like. A normal or expected AFE value may be determined by utilizing at least a portion of previously collected sensor data. What is considered to be a normal or expected AFE value may also vary by sensor, by sensor parameter, or by other parameters/characteristics that may be factored into what is determined to be normal or expected (e.g., the subject, the activity the subject is engaged in).

Once an outlier is identified, the pre-filter logic then uses a backward fill method to fill the one or more outliers (i.e., AFE values that fall outside of the accepted lower and upper bound) with the next value available that falls within the normal range in the current window of samples. This results in a cleaner and more predictable time-series of values which is devoid of un-processable noise. In a refinement, the one or more values are produced by utilizing artificial intelligence or machine learning techniques in which the model has been trained to predict the next AFE value given a past sequence of AFE values, and/or as a replacement to one or more outliers in order to enable the sequence of values to fall within a normal range. In a variation, a user could utilize a heuristic or mathematical formula-based method that describe waveforms similar to what an AFE signal produced from a sensor would be.

For heart rate values, the system may increase the amount of data used by the pre-filter logic processing the raw data to include n number of seconds worth of AFE data. An increase in the amount of data collected and utilized by the system enables the system to create a more predictable pattern of HR generated values as the number of intervals that are used to identify the QRS complex is increased. This occurs because HR is an average of the HR values calculated over one second sub-intervals. The n number of seconds is a tunable parameter that may be pre-determined or dynamic. In a refinement, artificial intelligence or machine learning techniques may be utilized to predict the n number of seconds of AFE data required to generate one or more values that fall within a given range based on one or more previously collected data sets.

While the pre-processing of the data may not replicate the possible R-peaks in a QRS complex, the pulling in of one or more noisy values into the range of a normal or expected signal allows the downstream filter and system generating the HR values to produce one or more HR values that fall within the expected range in absence of a quality signal.

Over the past many years, heart rate has been widely used in medical as well as consumer health monitoring systems. Heart rate is a non-invasive measure of autonomic nervous system (ANS). Heart rate and monitoring is effectively used in sports for the training and evaluation of any given performance. It also provides insights related to aerobic fitness. Heart rate is also used in a wide variety of applications such as optimizing training and recovery, the identifying of risk of disease, health monitoring, mortality and morbidity, and the like. In addition, heart rate measurements coupled with other data sets or inferences may provide additional value as it relates to heart rate interpretation. For example, numerous factors can impact heart rate measurements, including strain and recovery, which may lead to multiple interpretations of the same data. Furthermore, information related to the context in which the heart rate measurements are captured may be relevant (e.g., heart rate measurements captured at the beginning of a training program vs the middle; physical exertion distribution; training load), as well as other sensor data collected (e.g., muscle-related data, hydration-related data) and observations (e.g., perceived fatigue).

Real-time or near real-time monitoring of heart rate measurements and/or its one or more derivatives may be used in a number of applications and in a wide variety of industries including aviation and space travel, medical (e.g., hospitals), pharmaceutical, automotive, military, sports, fitness, municipality (e.g., police, firefighters), healthcare, finance, insurance, manufacturing, telecom, food & beverage, ICT, oil & gas, personal wellness, research, corporate wellness, and the like. For example, a trainer or fitness technology (e.g., fitness machine) may adjust an athlete's exercise pattern during training based on the computed heart rate. During training or competition, an athlete may be rested based on a heart rate indicating fatigue, sub-optimal performance or risk of injury. Heart rate and/or its one or more derivatives may be utilized as part of an indicator for markers such as energy exertion or stress. The heart-based measurements and/or its one or more derivatives may be utilized within sports betting applications as, at least in part, a wager/bet, as information to be used to place a wager/bet, as information to adjust the odds related to a wager/bet, as an input to create a betting product, as an input to evaluate or calculate a probability (e.g., the likelihood that an individual will have a heart attack), as an input in the formulation of a strategy (e.g., whether or not an insurance company wants to insure a specific person based on their heart-based measurements), as an input to mitigate a risk (e.g., for an insurance company, utilizing heart-based data to decide not to insure someone or raise a premium based upon heart-based data; for a hospital, monitoring heart-based measurements to ensure a person does not have a heart attack; for space travel, monitoring heart-based data to determine the suitability of a subject for space travel), as an input in media content (e.g., using heart-based measurements generated from your group fitness class to share across your social media or a fitness company's online community; using heart rate data as part of a live broadcast for professional sports or video gaming content), or as an input in a promotion. Additional details related to an Animal Data Prediction System with applications that may utilize one or more heart rate measurements and/or its one or more derivatives are disclosed in U.S. Pat. No. 62/833,970 filed Apr. 15, 2019 and U.S. Pat. No. 62/912,822 filed on Oct. 9, 2019; the entire disclosures of which are hereby incorporated by reference.

In a variation, at least a portion of the one or more heart-based measurements and/or its one or more derivatives are used to monitor, or provide feedback directly or indirectly related to, the health of one or more users in real-time or near real-time. For example, one or more subjects may want to monitor their own heart rate-based measurements in a number of different environments throughout the day (e.g. in their home, while at work, while at a fitness class, while sleeping), with the heart rate and/or its one or more derivatives (e.g., performance zones) being displayed in real-time or near real-time. In another example, an airline may want to monitor the heart rate or ECG of their pilots to better understand their physiological conditions while flying. A space travel company may want to monitor real-time heart-based measurements of its passengers or crew as part of health-related, in-flight status checks. An insurance company may want heart rate measurements during exercise or other activity to better understand the physiological characteristics of an individual it may insure, and adjust a premium based on that data. A construction company or oil & gas company may want to monitor the real-time heart health of its workers. A military organization may want to monitor the real-time health of its soldiers. A retirement facility or nursing home may want to monitor the heart rate measurements for its patients. A taxi company may want to monitor the physiological data related to its drivers for insurance purposes. A corporation may want to monitor the real-time heart rate of its employees while at work. A fitness platform, such as a combined bicycle with monitor/display, treadmill with monitor/display, or software analytics platform, may want to provide real-time heart rate feedback to users of its platform during a workout or before or after a workout. In these examples, monitoring in one or more locations may occur via direct communication between the one or more sensors that derive the heart-based measurements and an application executed within a web browser. Additional details related to a browser-based Biological Data Tracking System and Method with applications to heart rate measurements and/or its one or more derivatives are disclosed in U.S. patent Ser. No. 16/274,701 filed on Feb. 13, 2019; the entire disclosure of which is hereby incorporated by reference. In a refinement, the display, which communicates the one or more heart rate measurements and/or its one or more derivatives to one or more users, provides one or more recommendations, instructions, or directives for one or more actions to be taken by the one or more users based upon at least a portion of the one or more heart-based measurements and/or its one or more derivatives. For example, the display device may provide one or more recommendations for one or more actions to be taken based upon the data (e.g., "stop your activity" if the heart rate measurements are too high; "see a doctor" if the heart rate measurements or ECG are irregular; an action to call an emergency number is initiated or a "Call Emergency Number" alert provided on the display device to a user, e.g., spouse or doctor of the subject, if a subject's heart rate measurements signal a potential health issue).

In a refinement, one or more adjustments, changes, modifications, or actions are recommended, initiated, or taken based upon at least a portion of the subject's one or more heart-based measurements and/or its one or more derivatives. For example, a user (e.g., an automotive company) may want to monitor heart rate or ECG measurements of a driver or passenger in a vehicle to determine a status or condition of the subject within the vehicle. The user or the vehicle itself may take one or more corrective actions (e.g., stop the car, pull the car over) should one or more heart rate measurements be interpreted to signal one or more potential issues with the driver and/or passenger (e.g., if a passenger has a heart attack). In another example, a fitness platform (e.g., application, interconnected fitness hardware and software) that monitors a subject's heart rate may make an adjustment in real-time or near real-time based on the heart rate measurements and/or its one or more derivatives (e.g., a treadmill may autonomously slow down or speed up automatically based on heart-based target goals; a stationary bicycle may autonomously increase or decrease difficulty based upon a subject's heart rate). In another example, an integrated computing and display device may take the action to call 911 if a person is detected to have irregular measurements. In yet another example, an insurance company may apply any of the systems set forth above to adjust a premium based upon a subject's heart-based measurements and/or its one or more derivatives.

In a refinement, one or more subjects may receive consideration in exchange for providing access to at least a portion of their heart rate measurements and/or its one or more derivatives. For example, an athlete may provide access to their heart rate measurements and/or its one or more derivatives for public consumption (e.g., to show their heart rate data in a live sports broadcast) in exchange for consideration (e.g., money or something of value). In another example, a person who meets the criteria of a research organization interested in collecting heart rate measurements from a particular subset of people (e.g., defined age, weight, height, medical conditions, social habits, etc.) may provide the research organization with access to their heart rate measurements as part of a larger group study (e.g., the study requires 10,000 individuals, and this person is 1 of 10,000) in exchange for consideration. In another example, one or more users of a fitness platform, such as a combined bicycle/monitor, treadmill/monitor, fitness machine, or software analytics platform, may provide its collected heart rate measurements and/or its one or more derivatives to one or more parties interested in acquiring the data (e.g., insurance company) in exchange for consideration provided back to the user (e.g., data creator) or data rights holder (e.g., owner), which could be monetary in nature or provided in another form (e.g., discounted or free access to the fitness platform, a lower insurance premium, other free or discounted perks). Additional details of a Monetization System for Human Data with applications to heart rate measurements and/or its one or more derivatives are disclosed in U.S. Pat. No. 62/834,131 filed Apr. 15, 2019 and U.S. Pat. No. 62/912,210 filed Oct. 8, 2019; the entire disclosures of which is hereby incorporated by reference.

In a refinement, at least a portion of the one or more heart-based measurements and/or its one or more derivatives are used (1) to formulate one or more strategies; (2) to provide one or more markets upon which one or more wagers/bets can be placed; (3) to inform one or more users to take an action; (4) as one or more values upon which one or more wagers/bets are placed; (5) to calculate, modify, or evaluate one or more probabilities or odds; (6) to create, enhance, or modify one or more products; (7) as one or more data sets or as part of another one or more data sets utilized in one or more simulations, applications, or analyses; (8) within one or more simulations, the output of which directly or indirectly engages with one or more users; (9) as an input in one or more media or promotions; or (10) to mitigate one or more risks. Products can include data products that can be acquired, bought, sold, traded, licensed, advertised, rated, standardized, certified, leased, or distributed.

In another refinement, the heart rate measurements and/or its one or more derivatives may be utilized to create artificial data, which may be generated via one or more simulations and based upon at least a portion of the heart rate measurements and/or its one or more derivatives. The artificial data can be used for a number of applications including (1) to formulate one or more strategies; (2) to provide one or more markets (e.g., proposition bets) upon which one or more wagers/bets can be placed; (3) to inform one or more users to take an action; (4) as one or more values upon which one or more wagers/bets are placed; (5) to calculate, modify, or evaluate one or more probabilities or odds; (6) to create, enhance, or modify one or more products; (7) as one or more data sets or as part of another one or more data sets utilized in one or more simulations, applications, or analyses; (8) within one or more simulations, the output of which directly or indirectly engages with one or more users; (9) as an input in one or more media or promotions; or (10) to mitigate one or more risks. Advantageously, artificial data derived from, at least in part, heart rate measurements may be utilized to predict future occurrences or trends. Artificial data may be generated utilizing one or more artificial intelligence and/or machine learning techniques that may involve the training of one or more neural networks.

In another refinement, one or more trained neural networks are able to utilize previously collected ECG-derived data such as heart rate measurements to identify and/or categorize one or more variations in the data (e.g., "valid" R-Peak vs "false" R-Peak detection) in order to provide more precise and accurate heart rate measurements. For example, if one or more ECG data sets has been collected for an individual in any given activity, the one or more neural networks may be trained to identify and differentiate between a valid R-Peak and a false R-Peak (or noisy R-Peak). Furthermore, the one or more neural networks may be trained to generate artificial heart rate measurements or other ECG-related data that is based upon real heart rate measurements or ECG-related data collected. For example, if one or more data sets related to heart rate measurements has been collected by the system for any given activity, the one or more neural networks may be trained to generate artificial data (e.g., heart rate measurements) to predict future occurrences by having the ability to adjust one or more variables. If physiological data sets, including heart rate measurements, for any given athlete have been collected with one or more variables (e.g., 85 degree temperature, 65% humidity, 2000 ft elevation), the system may have the ability to generate artificial data (e.g., artificial heart rate measurements) that incorporates one or more adjusted variables set by a user (e.g., running a simulation to understand how the athlete's heart rate measurements will look in 95 degree heat vs 85 degree heat). The neural network may be trained utilizing any number of methods including a Generative Adversarial Network (GAN). A GAN is a deep neural network architecture comprised of two neural networks, pitting one against the other (adversarial). Utilizing a GAN, the generator generates one or more new data values, which may comprise one or more new data sets, while the discriminator evaluates the one or more new values based on one or more user-defined criteria to certify, validate, or authenticate the newly created values. Additional details of a System for Generating Simulated Animal Data And Models are disclosed in U.S. Pat. No. 62/897,064 filed Sep. 6, 2019; the entire disclosure of which is hereby incorporated by reference.

In a refinement, the one or more variables in the one or more simulations may be determined by one or more users, and the output of the one or more simulations may be distributed to the one or more users in exchange for consideration.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. As such, embodiments described as less desirable than other embodiments or prior art implementations with respect to one or more characteristics are not outside the scope of the disclosure and can be desirable for particular applications.

What is claimed is:

1. A system for measuring a heart rate, the system comprising:
   at least one sensor configured to measure electric signals in a subject's body, convert one or more analog measurements to one or more digital readings, and transmit the one or more digital readings;
   a server configured to receive the one or more digital readings and calculate heart rate based on one or more overlapping segments of the one or more digital readings by identifying R-peaks within the one or more overlapping segments, calculating one or more sample values based on times between adjacent R-peaks, discarding one or more samples that are influenced by false peak detection or missed peak detection, and calculating one or more averages of remaining sample values; and
   a display device configured to display the one or more averages of the remaining sample values.

2. The system of claim 1 wherein the server determines that one or more samples are influenced by false peak detection or missed peak detection in response to a given sample value differing from a previous heart rate value by more than a first threshold.

3. The system of claim 2 wherein, in response to a standard deviation of differences between one or more samples being greater than a second threshold, the server determines that the one or more samples are influenced by false peak detection or missed peak detection in response to the sample value differing from the previous heart rate value by more than a third threshold different than the first threshold.

4. The system of claim 3 wherein the third threshold is less than the second threshold.

5. The system of claim 1 wherein at least a portion of the one or more heart-based measurements and/or its one or more derivatives are used (1) to formulate one or more strategies; (2) to provide one or more markets upon which one or more wagers can be placed; (3) to inform one or more users to take an action; (4) as one or more values upon which one or more wagers are placed; (5) to calculate, modify, or evaluate one or more probabilities or odds; (6) to create, enhance, or modify one or more products; (7) as one or more data sets or as part of another one or more data sets utilized in one or more simulations, applications, or analyses; (8) within one or more simulations, the output of which directly or indirectly engages with one or more users; (9) as an input in one or more media or promotions; or (10) to mitigate one or more risks.

6. The system of claim 1 wherein at least a portion of the one or more heart-based measurements and/or its one or more derivatives are used to monitor, or provide feedback directly or indirectly related to, the health of one or more users in real-time or near real-time.

7. The system in claim 1 wherein the display device provides one or more recommendations, instructions, or directives for one or more actions to be taken by one or more users based upon at least a portion of the one or more heart-based measurements and/or its one or more derivatives.

8. The system in claim 1 wherein one or more adjustments, changes, modifications, or actions are recommended, initiated, or taken based upon at least a portion of a subject's one or more heart-based measurements and/or its one or more derivatives.

9. A system for measuring a heart rate, the system comprising:
   at least one sensor adapted for fixation to, or is in contact with, or sends an electronic communication in relation to or derived from, a subject's skin, vital organ, muscle, veins, blood, blood vessels, tissue, or skeletal system, and configured to measure one or more electric signals in a subject's body, convert analog measurements to one or more digital readings, and transmit the digital readings;
   a server configured to receive the one or more digital readings and calculate one or more heart rate values based on one or more overlapping segments of the one or more digital readings by identifying R-peaks within the one or more overlapping segments, calculating one or more sample values based on times between adjacent R-peaks, selecting one or more samples within a first threshold of a previous heart rate value, and setting a current heart rate value to an average of selected samples; and
   a display device configured to display one or more current heart rate values.

10. The system of claim 9 wherein the display device displays each current heart rate value before a respective succeeding heart rate value is calculated.

11. The system of claim 10 wherein the server calculates each current heart rate value before the at least one sensor completes measuring at least a portion of the one or more digital readings used to calculate a succeeding heart rate value.

12. The system of claim 9 wherein the server selects samples within a second threshold of the previous heart rate value in response to a standard deviation of differences between consecutive samples being greater than a third threshold.

13. The system of claim 9 wherein the server sets the current heart rate value equal to the previous heart rate value in response to the number of samples being less than a fourth threshold.

14. The system of claim 9 wherein the server sets the current heart rate value equal to the previous heart rate value in response to no samples being selected.

15. The system of claim 9 wherein each sample value is proportional to a reciprocal of a time between adjacent R-peaks.

16. The system of claim 9 wherein the server computes an initial heart rate value by receiving a preliminary segment of the digital readings longer than the one or more overlapping segments, identifying R-peaks within the preliminary segment, calculating sample values based on times between adjacent R-peaks, and calculating an average of the samples.

17. The system of claim 9 wherein one or more samples are artificially generated based upon at least a portion of a previously collected data and utilizing one or more artificial intelligence or machine learning techniques.

18. A method for measuring a heart rate of a person, the method comprising:
   receiving a first segment of digital readings from at least one sensor;
   identifying R-peaks within the first segment of digital readings;
   calculating a first plurality of sample values based on times between adjacent R-peaks;
   selecting a first subset of the first plurality of sample values including only sample values within a first threshold of a previous heart rate value;
   calculating a first updated heart rate value based on an average of the first subset of the first plurality of sample values; and
   displaying the first updated heart rate value.

19. The method of claim 18 further comprising:
   receiving a second segment of digital readings from at least one sensor;
   forming a third segment of digital readings by appending the second segment to the first segment of digital readings;
   identifying R-peaks within the third segment of digital readings;
   calculating a second plurality of sample values based on times between adjacent R-peaks;
   selecting a second subset of the second plurality of sample values including only sample values within the first threshold of the first updated heart rate value;
   calculating a second updated heart rate value based on an average of the second subset of the second plurality of sample values; and
   displaying the second updated heart rate value.

20. The method of claim 18 further comprising:
   receiving a second segment of digital readings from at least one sensor,
   forming a third segment of digital readings by appending the second segment of digital readings to the first segment of digital readings;
   identifying R-peaks within the third segment of digital readings;
   calculating a second plurality of sample values based on times between adjacent R-peaks;
   calculating a plurality of differences between consecutive samples;
   in response to a standard deviation of the differences exceeding a second threshold, selecting a second subset of the second plurality of sample values including only sample values within a third threshold of the first updated heart rate value;
   calculating a second updated heart rate value based on the average of the second subset of the second plurality of sample values; and
   displaying the second updated heart rate value.

21. The method of claim 18 wherein calculating the first plurality of sample values comprises dividing a constant by times between adjacent R-peaks.

22. The method of claim 18 further comprising computing an initial heart rate value by:
   receiving a preliminary segment of digital readings;
   identifying R-peaks within the preliminary segment of digital readings;
   calculating sample values based on times between adjacent R-peaks; and
   calculating an average of the sample values.

23. A method for detecting and replacing one or more outlier values generated from one or more sensors, the method comprising:

receiving one or more values generated directly or indirectly by the one or more sensors;

applying one or more statistical tests to determine an acceptable upper and/or lower bound for each value; and utilizing a backward filling method to replace the one or more outlier values with a next available value that falls within an acceptable range established in a current window of samples.

24. The method in claim 23 wherein detection of the one or more outlier values and/or establishment of an upper and/or lower bound take into account at least one of the following variables: one or more characteristics of a subject, type of sensor, one or more sensor parameters, one or more sensor characteristics, one or more environmental factors, or one or more activities the subject is engaged in.

25. The method in claim 24 wherein detection of the one or more outlier values occurs or an upper and/or lower bound are created or adjusted, at least in part, utilizing one or more artificial intelligence or machine learning techniques that use at least a portion of previously collected sensor data and/or its one or more derivatives and at least one variable.

26. The method in claim 23 wherein one or more artificial intelligence or machine learning techniques are used, at least in part, to generate one or more artificial values within the upper and lower bound derived from at least a portion of previously collected sensor data and/or one or more derivatives thereof.

* * * * *